(12) United States Patent
Banco et al.

(10) Patent No.: US 9,783,357 B2
(45) Date of Patent: Oct. 10, 2017

(54) METHODS FOR EMITTING AND REFILLS FOR HOLDING TWO OR MORE COMPOSITIONS

(71) Applicant: S. C. Johnson & Son, Inc., Racine, WI (US)

(72) Inventors: Michael J. Banco, Racine, WI (US); Nathan R. Westphal, Union Grove, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 167 days.

(21) Appl. No.: 14/676,283

(22) Filed: Apr. 1, 2015

(65) Prior Publication Data

US 2016/0288979 A1   Oct. 6, 2016

(51) Int. Cl.
| | |
|---|---|
| *A61L 9/00* | (2006.01) |
| *B65D 81/32* | (2006.01) |
| *A61L 9/02* | (2006.01) |
| *F24F 3/16* | (2006.01) |
| *A01M 1/20* | (2006.01) |
| *A61L 9/03* | (2006.01) |
| *A61L 9/12* | (2006.01) |

(52) U.S. Cl.
CPC .......... *B65D 81/32* (2013.01); *A01M 1/2022* (2013.01); *A61L 9/02* (2013.01); *A61L 9/03* (2013.01); *A61L 9/035* (2013.01); *A61L 9/12* (2013.01); *A61L 9/125* (2013.01); *F24F 3/16* (2013.01); *F24F 2003/1689* (2013.01)

(58) Field of Classification Search
CPC ........ B65D 81/32; A01M 1/2022; A61L 9/02; A61L 9/03; A61L 9/035; A61L 9/12; F24F 3/16

USPC ...................................................... 239/34–60
See application file for complete search history.

(56) References Cited

U.S. PATENT DOCUMENTS

| | | |
|---|---|---|
| 6,968,124 B1 | 11/2005 | Varanasi |
| 7,014,819 B2 | 3/2006 | Hart et al. |
| 7,032,831 B2 | 4/2006 | Duston |
| 7,055,764 B1 | 6/2006 | Martinez et al. |
| 7,329,636 B1 | 2/2008 | Golz-Berner et al. |
| 7,819,336 B2 | 10/2010 | Newman |

(Continued)

FOREIGN PATENT DOCUMENTS

WO   WO 2011092428   8/2011

OTHER PUBLICATIONS

PCT/US2016/024825 International Search Report & Written Opinion. Dated May 13, 2016.

*Primary Examiner* — Arthur O Hall
*Assistant Examiner* — Viet Le

(57) ABSTRACT

A refill for holding at least two compositions comprises a container including a body and first and second compositions disposed within the body such that the first and second compositions are substantially separated and the second composition is disposed above the first composition. The refill further includes a tube disposed within the body of the container such that the tube contains the first and second compositions, wherein the tube has an inner diameter and an outer diameter. Still further, the refill includes a wick disposed within the tube, wherein the wick contains the first and second compositions and has a diameter that is smaller than the inner diameter of the tube to create a gap between the wick and the tube.

20 Claims, 7 Drawing Sheets

(56) References Cited

U.S. PATENT DOCUMENTS

| | | |
|---|---|---|
| 7,840,123 B2 | 11/2010 | Belongia |
| 2003/0194225 A1 | 10/2003 | Pedrotti |
| 2004/0065749 A1 | 4/2004 | Kotary et al. |
| 2005/0180736 A1 | 8/2005 | Zobele |
| 2006/0175425 A1 | 8/2006 | McGee et al. |
| 2008/0251599 A1 | 10/2008 | Ward et al. |
| 2009/0101729 A1* | 4/2009 | Newman ............... A61L 9/127 239/44 |
| 2010/0187327 A1* | 7/2010 | Irvin ................... A61L 9/125 239/47 |
| 2011/0049259 A1 | 3/2011 | Beland |
| 2011/0139885 A1* | 6/2011 | Gasper ................. A61L 9/037 239/6 |

* cited by examiner

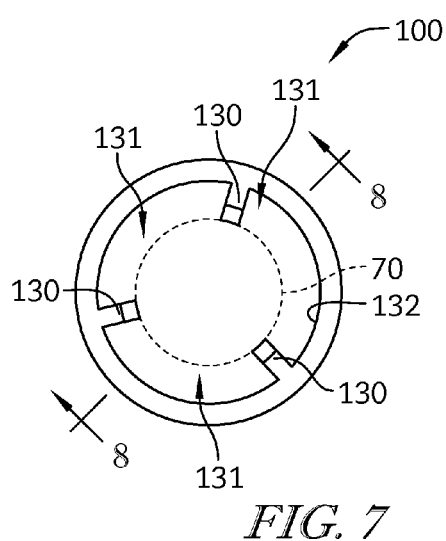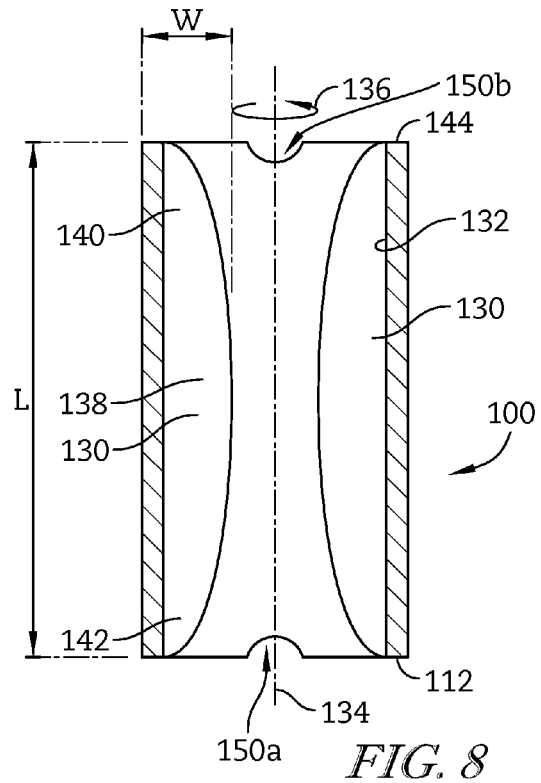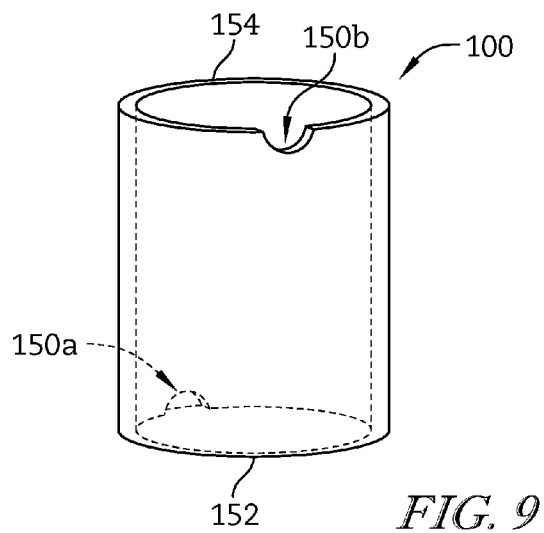

METHODS FOR EMITTING AND REFILLS FOR HOLDING TWO OR MORE COMPOSITIONS

BACKGROUND

1. Field of the Disclosure

The present disclosure relates generally to methods and systems for emitting compositions and, more particularly, to methods and systems for emitting two or more compositions.

2. Description of the Background

It is known that the perception of a user of a dispensed fragrance at a constant intensity tends to decay over time. This decay in perception, which is commonly referred to as adaptation and/or habituation, reduces the enjoyment of the dispensed fragrance by the user. Adaptation and/or habituation are the reduction of physiological, psychological, or behavioral response occurring when a specific stimulus occurs repeatedly. It is generally believed that adaptation and/or habituation with respect to a fragrance can be reduced by changing the level of intensity of the dispensed fragrance or by dispensing a different fragrance. Fragrance dispensers and methods of dispensing fragrances that address the issue of adaptation and/or habituation are known in the art.

One such fragrance dispenser emits a first fragrance from a first refill for a first period of time followed by emission of a second fragrance from a second refill for a second period of time followed by emission of a third fragrance from a third refill for a third period of time. A further pattern or algorithm for dispensing fragrances includes emission of a first fragrance from a first refill in repeated short intermittent bursts during a first period of time, the emission of a second fragrance from a second refill in repeated short intermittent bursts during a second period of time, and the emission of a third fragrance from a third refill in repeated short intermittent bursts during a third period of time. In any of the above-described patterns or algorithms, one or more fans, heaters, or any suitable devices may be utilized to facilitate emission of each of the fragrances.

Another dispenser emits fragrances in an alternating sequence while the dispenser is activated. The dispenser includes, for example, first and second heaters for emitting first and second fragrances, respectively, from first and second refills, respectively. In one embodiment, the fragrances are alternatively emitted by deactivating one of the heaters at the same time the other of the heaters is activated. Alternatively, one of the heaters may be deactivated followed by a gap period and then the other of the heaters may be activated. Still further, one of the heaters may be activated before the other of the heaters is deactivated to create an overlap period. Existing devices offering solutions to adaptation and/or habituation may change dispensed fragrances or intensities thereof frequently over a period of a day or several hours, for example, every 45 minutes, thereby exposing a user to a seemingly constant change of fragrance.

Current multi-fragrancing devices require multiple refills and/or multiple actuators for emitting different fragrances. Multiple refills and/or multiple actuators increase the footprint and/or overall size of a dispenser from which the fragrances are emitted and/or increase the overall cost of the dispenser.

SUMMARY

In illustrative embodiments, a method of emitting two or more compositions may comprise the step of providing a refill including a container having a body and first and second compositions disposed within the body such that the first and second compositions are substantially separated. The method may further include the steps of emitting a first portion of the second composition, emitting a portion of the first composition after the first portion of the second composition is emitted, and emitting a second portion of the second composition.

In some embodiments, the step of emitting a portion of the first composition may include emitting substantially all of the first composition.

In some embodiments, the step of emitting a second portion of the second composition may include emitting the second composition until substantially all of the second composition is depleted.

In some embodiments, the first portion of the second composition may be emitted from within the tube, a portion of the first composition may be emitted from within the tube and a remainder of the first composition may be emitted from within the container, and the second portion of the second composition may be emitted from within the container.

In some embodiments, the method may further include the step of providing a dispenser including a housing forming a chamber adapted to retain the refill containing two or more compositions and a heater disposed within the chamber.

In some embodiments, the second composition may be disposed above and substantially separated from the first composition.

In illustrative embodiments, a refill for holding at least two compositions may include a container including a body and first and second compositions disposed within the body such that the first and second compositions are substantially separated and the second composition is disposed above the first composition. The refill may further include a tube disposed within the body of the container such that the tube contains the first and second compositions, wherein the tube may have an inner diameter and an outer diameter. A wick may be disposed within the tube, wherein the wick contains the first and second compositions and has a diameter that is smaller than the inner diameter of the tube to create a gap between the wick and the tube.

In some embodiments, the tube may have a volume that is between about 5% and about 50% of a volume of the body of the container.

In some embodiments, at least two ribs may extend inwardly from an inner peripheral surface of the tube and extend across the gap to center the wick and retain the wick within the tube.

In some embodiments, the refill may further include a first vent disposed in an upper peripheral edge of the tube and a second vent disposed in a lower peripheral edge of the tube.

In some embodiments, the first and second vents may be disposed at about 180 degrees with respect to one another.

In some embodiments, the refill may include a metering orifice or slot disposed through the tube to form a metering opening.

In some embodiments, the tube may include an inner tube and an outer tube that are configured to be rotated with respect to one another.

In some embodiments, the inner tube may include a first orifice and the outer tube includes a second orifice and the inner and outer tubes are configured to be rotated with respect to one another to open or partially open the first and second orifices.

In some embodiments, the first and second orifices may be disposed through bottom walls of the inner and outer tubes, respectively, a third orifice may be disposed through a side wall of the inner tube, and a fourth orifice may be disposed through a side wall of the outer tube, and rotation of the inner and outer tubes may fully or partially open the third and fourth orifices.

In some embodiments, either the first and second orifices may be opened or the third and fourth orifices may be opened, but both the first and second orifices and the third and fourth orifices may not be opened at the same time.

In illustrative embodiments, a method of assembling a refill having a container including a body for holding at least two compositions may include the step of filling the body of the container with first and second different compositions such that the first and second materials are substantially separated and the second composition is disposed above the first composition. The method may further include the steps of inserting a tube through the neck of the container and into the body such that the tube is filled with the first and second compositions and inserting a wick into the tube, wherein an outer diameter of the wick is smaller than an inner diameter of the tube such that a gap is created between the tube and the wick.

In some embodiments, the second composition within the wick may be disposed above the first composition within the wick.

In some embodiments, the tube may include one or more features selected from the group consisting of: a vent, a metering hole, a metering slot, and one or more ribs.

In some embodiments, the step of filling the body may include filling the body with first, second, and third different compositions and, during the step of inserting the tube, the tube may be filled with the first, second, and third compositions.

BRIEF DESCRIPTION OF THE DRAWINGS

FIG. 7 is a top elevational view of an embodiment of a tube for use with a refill of the present disclosure;

FIG. 8 is a cross-sectional taken generally along the lines 8-8 of FIG. 7;

FIG. 9 is a top isometric view of a further embodiment of a tube for use with a refill of the present disclosure;

Other aspects and advantages of the present disclosure will become apparent upon consideration of the following detailed description, wherein similar structures have like or similar reference numerals.

DETAILED DESCRIPTION

The present disclosure is directed to methods and systems for emitting two or more compositions. While the methods and systems of the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Figure 1:
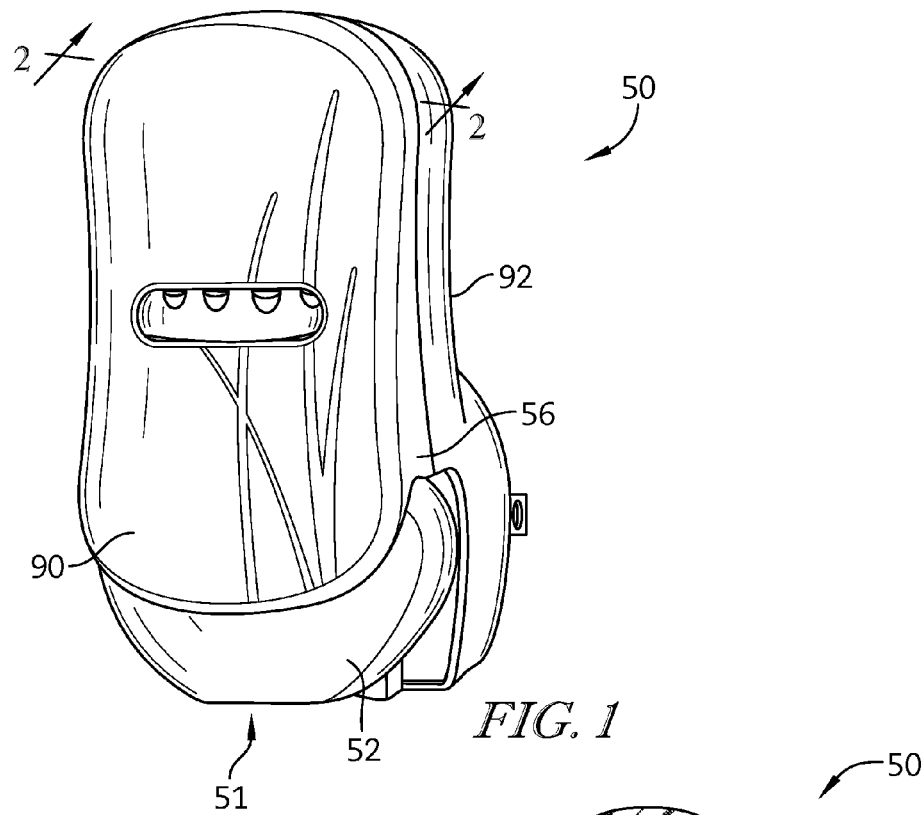
FIG. 1 is a top isometric view of an exemplary volatile material dispenser with which refills of the present invention may be utilized.
Figure 2:
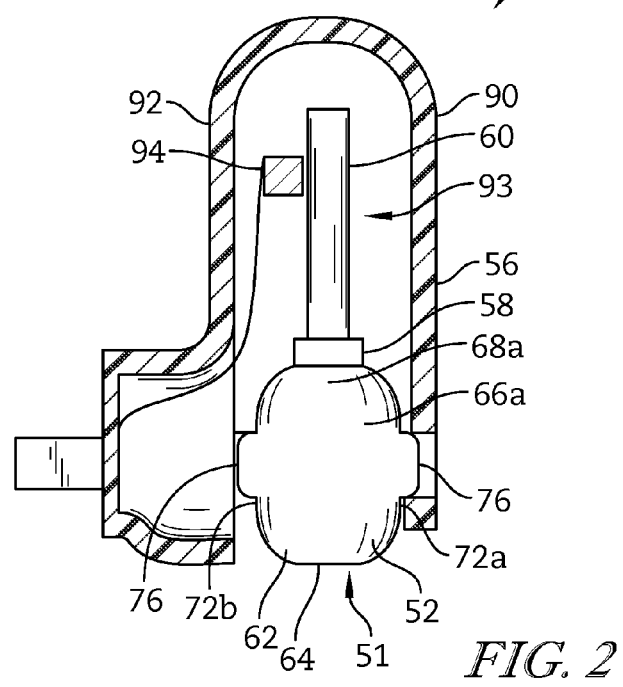
FIG. 2 is partial cross-sectional view taken generally along the lines 2-2 of FIG. 1 with the volatile material dispenser shown in cross-section and a refill shown in elevation.
Figure 3:
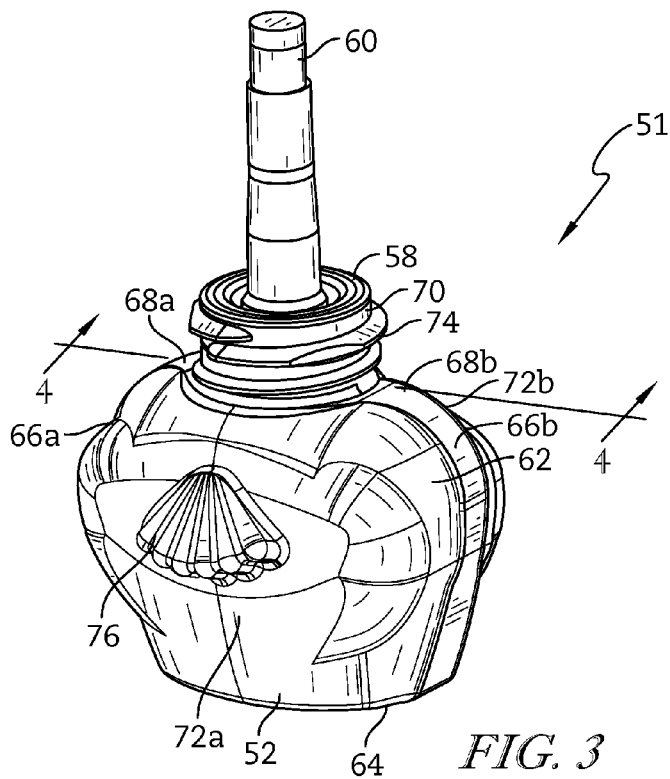
FIG. 3 is a top isometric view of an exemplary refill with which the principles of the present disclosure may be utilized.

Referring to the drawings, FIGS. 1 and 2 depict a volatile material dispenser 50 adapted to accommodate, for example, a refill 51, as seen in FIGS. 2-5. The refill 51 includes a container 52 that may include at least two compositions, for example, first and second compositions 53, 54, wherein the container 52 is adapted to be retained within a housing 56 of the volatile material dispenser 50. The container 52 includes a retaining mechanism 58 to hold a wick 60 within the container 52 and further includes a body 62 for holding the compositions 53, 54. The body 62 includes a base portion 64 and first and second opposing sidewalls 66a, 66b that extend upwardly and outwardly prior to curving inwardly toward first and second top walls 68a, 68b, respectively. Similarly, third and fourth opposing front and rear walls 72a, 72b, respectively, curve upwardly toward the neck 70. The first and second top walls 68a, 68b may be integral with a neck 70.

The neck 70 may include a threaded portion 74 disposed on an outer surface thereof and an opening (not shown) disposed through a top portion thereof, wherein the opening allows access to the compositions 53, 54. The container 52 may further optionally include raised portions 76 extending outwardly from one or more of the third and fourth opposing front and rear walls 72a, 72b. In one embodiment, the raised portions 76 are in the form of inverted shell-shaped members. Optionally or additionally, the refill 51 may include any suitable features, for example, for retention in a dispenser. Although a specific dispenser 50 and container 52 are described with particularity, it is contemplated that the principles of the present disclosure may be implemented with respect to any type of electrical or non-electrical dispenser and any type of refill. For example, dispensers useful for the present disclosure include, but are not limited to, the dispensers described in Belongia et al. U.S. Pat. No. 7,840,123, Varanasi et al. U.S. Pat. No. 6,968,124, Beland et al. U.S. Patent Application Publication No. 2011/0049259, Zobele U.S. Patent Application Publication No. 2005/0180736, and Pedrotti et al. U.S. Patent Application Publication No. 2003/0194225. Further, refills useful for the present disclosure include, but are not limited to, the containers described in U.S. Pat. No. 7,032,831, and the containers described in U.S. patent application Ser. No. 12/969,261, filed on Dec. 15, 2010, both of which are owned by the same assignee as the present invention.

Figure 4:
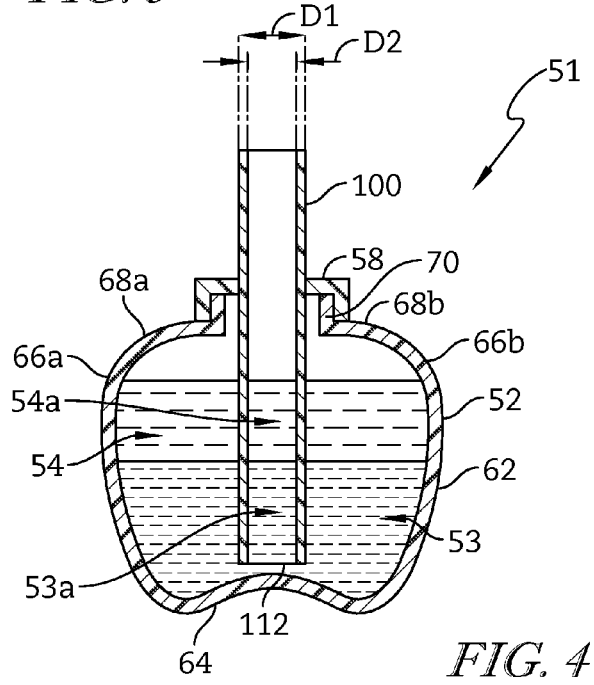
FIG. 4 is a cross-sectional view taken generally along the lines 4-4 of the refill of FIG. 3 with a wick removed therefrom.
Figure 5:
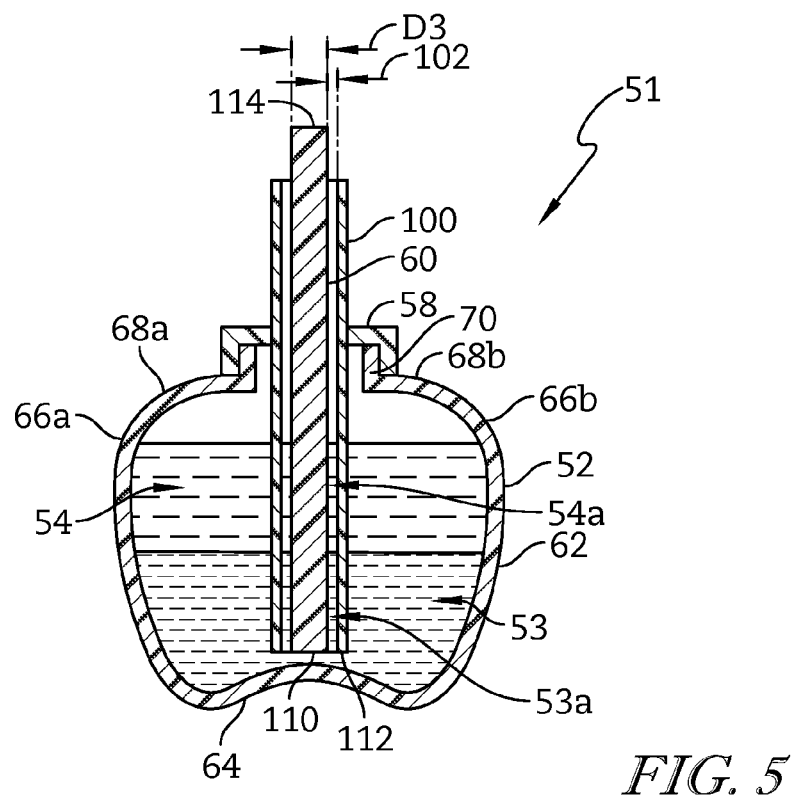
FIG. 5 is a cross-sectional view similar to the view of FIG. 4 and depicting the refill with a wick inserted therein.

Two or more different compositions may be held within the body 62 of the container 52, as seen in FIGS. 4 and 5. The first composition 53 and the second composition 54 may be layered within the body 62, for example, with the first composition 53 below the second composition 54. The first and/or second compositions 53, 54 may be any suitable liquid or liquids and one or both of the compositions 53, 54 may include one or more active ingredients. Exemplary active ingredients include, but are not limited to, one or more of a cleaner, an insecticide, an insect repellant, an insect attractant, a disinfectant, a mold or mildew inhibitor, an antimicrobial, a fragrance comprised of one or more aroma chemicals, a disinfectant, an air purifier, an aromatherapy scent, an antiseptic, an odor eliminator, a positive fragrancing active material, an air-freshener, a deodorizer, a medicinal component, an inhalant (e.g., for relieving a cough or congestion), or the like, and combinations thereof. Additives may be included in the composition, such as, for example, fragrances and/or preservatives. Regardless of the specific compositions, the first and second compositions 53, 54 may be the same or different.

One or more of the compositions utilized in the refill 51 may include one or more dyes of any suitable color or colors. In this manner, if each composition takes on a different color (or no color), the compositions may be visible to a user as distinct layers of material within the container 52 (and/or wick 60) and tube, which is discussed in detail below. In an illustrative embodiment, if the first composition 53 contains a first dye of a first color and the second composition 54 contains a second dye of a second color different than the first color, a user may be able to discern from the first and second colors how much of each composition 53, 54 remains in the refill 51 and which composition 53, 54 is being emitted. Additionally, during transition between compositions, the first and second colors may mix to form a third, different color to indicate a transition between the compositions. If more than two compositions are utilized, different dyes of different colors (or no color) may be utilized for each composition.

In illustrative embodiments, the first composition 53 is denser than the second composition 54 such that the first and second compositions 53, 54 form two distinct layers within the body 62 of the container 52. In illustrative embodiments, the first composition 53 may be a water-based composition that contains one or more active ingredients, for example, a fragrance, and the second composition 54 may be an oil-based fragranced composition. In alternative embodiments, the first or second compositions 53, 54 may both be water-based or oil-based (with different densities) and/or one of the compositions 53, 54 may not include any active materials (for example, one composition may be water).

It should be understood that any densities may be utilized with the concepts of the present disclosure. In the illustrative embodiment described above, first and second compositions 53, 54 of different densities create two distinct layers, wherein the first and second compositions 53, 54 are substantially separated. In this manner, the compositions 53, 54 may be sequentially emitted. If more than two compositions are used, each of the compositions may form a separate layer within the refill 51 for sequential emission thereof.

The compositions 53, 54 may have one or more of the same active materials or may have all different active materials. In illustrative embodiments, a change in emission from one of the compositions 53, 54 to the other of the compositions 53, 54 provides an increase in noticeability of the active ingredients, for example, fragrances. In one embodiment, the compositions 53, 54 may include different, distinct fragrances that provide a noticeable difference between the compositions 53, 54. In another embodiment, the compositions 53, 54 may include the same or similar fragrances with the fragrance(s) in one of the compositions 53, 54 being much stronger (for example, by having a greater weight percentage of fragrance(s) that the other of the compositions 53, 54) to provide a noticeable difference between the compositions 53, 54.

Now turning generally to FIGS. 1 and 2, the housing 56 of the volatile material dispenser 50 includes front and rear portions 90, 92 attached to one another to form a chamber 93 therebetween. The container 52 may be inserted into the housing 56 by inserting the wick 60 upwardly into the chamber. The container 52 may be retained within the housing 56 by conventionally known means, including a snap-fit connection, a threaded interaction, and the like. In illustrative embodiments, a portion of the wick 60 may be disposed adjacent a heater 94 (see FIG. 2) that is disposed in the housing 56. A top and/or a front portion of the housing 56 may include an opening for release of the compositions including one or more active materials therethrough. As noted above, the dispenser 50 may be any dispenser 50 for insertion into a conventional electrical socket, operated by one or more batteries, or may be passive and/or the dispenser 50 may include any number of adjustment features, vents, or other features, as known in the art.

In an illustrative embodiment of a refill 51, a tube 100 is disposed around at least a portion of the wick 60 disposed within the container 52 with a gap 102 formed between the tube 100 and the wick 60, as seen in FIGS. 4 and 5. More specifically, the tube 100 has an outer diameter D1 and an inner diameter D2 forming a thickness of the tube 100 and the wick 60 has an outer diameter D3. The inner diameter D2 of the tube 100 is greater than an outer diameter D3 of the wick 60 to create the gap 102. In illustrative embodiments, the gap 102 may be of any suitable dimensions that provide the gap 102 with a volume between about 5% and about 50% of a volume of the container 52. In an illustrative example, if a container 52 can hold up to 20 milliliters of liquid, the gap 102 may hold between about 1 milliliter and about 10 milliliters of liquid. In illustrative embodiments, the tube 100 may be integral with or otherwise connected to the retaining mechanism 58 that holds the wick 60 in place within the container 52 and/or closes the neck 70 of the container 52. The tube 100 may be made of a polymeric material, such as, for example, polyethylene, polypropylene, cross-linked polyethylene, other polymers, other suitable materials, or combinations thereof.

The tube 100 may be a separate component, may be attached to the wick 60, and/or may be integral with or attached to one or more of the container 52, the body 62, the retaining mechanism 58, the wick 60, a wick holder, a sheath surrounding the wick 60, and/or any other component of the refill 51.

In an illustrative embodiment, during assembly of the refill 51, the body 62 of the container 52 is filled (for example, through the neck 70) by pouring or otherwise transferring the first and second compositions 53, 54 into the body 62. Since the first composition 53 is denser than the second composition 54, the order in which the compositions 53, 54 are transferred into the body 62 is not very relevant, as the compositions 53, 54 will eventually settle (i.e., reach equilibrium) with the first composition 53 disposed below the second composition 54. As noted above, the first and second compositions 53, 54 have different densities such that the first and second compositions 53, 54 are substantially separated from one another. One skilled in the art will understand that there may be minor mixing of the compositions 53, 54 at an interface between the compositions 53, 54. If more than two compositions are utilized and have different densities, the compositions may be transferred into the body 62 in any suitable order, as the different compositions will settle (i.e., reach equilibrium) with the densest composition on the bottom and the least dense composition on the top.

After filling the body 62 with the compositions 53, 54, the tube 100 may be inserted through the neck 70 of the container 52 and into the body 62 such that the tube 100 is filled with the first and second volatile materials 53, 54. In illustrative embodiments, after insertion of the tube 100 into the body 62, as seen in FIG. 4, the tube 100 is filled with the first and second compositions 53, 54, for example, at 53a, 54a at levels that are similar to or the same as the levels of the compositions 53, 54 in the body 62. The compositions 53a, 54a within the tube 100 are also substantially separated, as are the compositions 53, 54 within the body 62. Once the tube 100 is inserted into the body 62 and filled with the compositions 53a, 54a, the wick 60 may be inserted into the tube 100. As the wick 60 is inserted into the tube 100, the wick 60 begins to absorb the compositions 53a, 54a. Even though a bottom end 110 of the wick 60 begins to absorb the second composition 54a first, once the wick 60 is fully inserted into the tube 100, for example, with the bottom end 110 of the wick 60 aligned with a bottom end 112 of the tube 100, the less dense second composition 54a rises to a level within the wick 60 that is above the more dense first composition 53a such that the first composition 53a is also disposed below the second composition 54a within the wick 60. As noted above, in illustrative embodiments, the outer diameter D3 of the wick 60 is smaller than the inner diameter of the tube 100. In this manner, the first and second compositions 53a, 54a are absorbed by the wick 60, but some of the first and second compositions 53a, 54a remain in the gap 102 between the tube 100 and the wick 60.

Optionally, the wick 60 and the tube 100 may be assembled (possibly even with the retaining mechanism 58) prior to insertion into the container 52. Once the wick 60, the tube 100, and/or the retaining mechanism 58 are assembled, they are inserted into the container 52. Depending on how quickly or slowly the assembly is inserted into the container 52, the wick 60 and the tube 100 may or may not include the first and second compositions 53a, 54a at generally the same level as the levels of the first and second compositions 53, 54 in the container 52.

In an illustrative method of emitting compositions from the refill 51, for example the compositions 53, 54, heat may be applied to the wick 60. In alternative illustrative embodiments, a fan, a piezoelectric element, or any other suitable activation element may be utilized to emit the compositions 53, 54 from the wick 60 or the compositions 53, 54 may be passively emitted (without any activation element) from the wick 60. During emission of the compositions 53, 54, the second composition 54a disposed within the wick 60 and the tube 100 is first emitted since it has a density less than the first composition 53a and is therefore closer to a top end 114 of the wick 60. Once the second composition 54a within the wick 60 and the tube 100 is substantially depleted, the first composition 53a within the wick 60 and the tube 100 is emitted. The wick 60 thereafter absorbs and emits the remainder of the first composition 53 disposed within the body 62 of the container 52 because the only access point to the wick 60 is the bottom end 110 of the wick 60 through a bottom end 112 of the tube 100. Lastly, after the first composition 53 has been substantially depleted, the second composition 54 within the body 62 is emitted until substantially depleted. One skilled in the art will understand that, at the time when the first composition 53 is almost depleted, there may be some mixing of the first and second compositions 53, 54 because the tube 100 and/or wick 60 may be spaced from the base portion 64 of the container 52 and/or because of minor mixing of the compositions 53, 54 at an interface between the compositions 53, 54.

Figure 6:
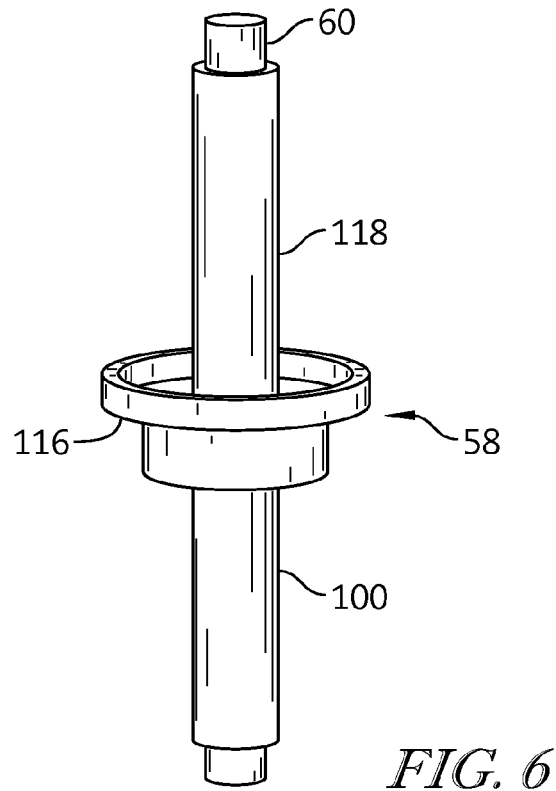
FIG. 6 is a top isometric view of a retaining mechanism including a cap portion and a sheath portion extending from the cap portion, a tube connected to or integral with the cap portion, and a wick held in position by the retaining mechanism and the tube.

As noted above, the tube 100 may be integral with or otherwise connected to (e.g., through a friction or interference fit) a retaining mechanism 58, as depicted in FIG. 6. The retaining mechanism 58 may include a cap portion 116 that may connect the retaining mechanism 58 to the neck 70 of the container 52 and/or a second sheath portion 118 that is integral with or otherwise connected to the cap portion 116 and extends outwardly from the cap portion 116. The sheath portion 118, if present, surrounds and protects a portion of the wick 60 that extends outside of the refill 51. The cap portion 116 may include any suitable features to retain the cap portion 116 on or within the neck 70 of the container 52 and/or may include any suitable features to retain the tube 100 and/or wick 60 within the cap portion 116. In some embodiments, the wick 60 may extend beyond the bottom end 112 of the tube 100 and/or a top of the sheath portion 118. In other embodiments, the wick 60 may extend to the bottom end 112 of the tube 100 and/or may include one or more vents as disclosed in detail hereinbelow. The tube 100 may optionally or alternatively include one or more ribs and/or one or more metering holes or orifices and/or slots, as described in detail below.

In an illustrative embodiment, any of the tubes disclosed herein, for example the tube 100 of FIGS. 4 and 5, may include one or more ribs 130 extending inwardly from an inner periphery 132 of the tube 100. While the exemplary embodiment of FIGS. 7 and 8 depicts three ribs 130, any suitable number of ribs 130 may be utilized. In illustrative embodiments, the ribs 130 are designed to slide onto the wick 60 without damage to the wick 60 and to create a friction or interference fit with the wick 60 to retain the wick 60 in position along a longitudinal axis 134 of the tube 100 and about a rotational axis 136 of the tube. In this manner, the ribs 130 may be utilized as an assembly tool to position the wick within the tube 100 and thereafter allow for insertion of the tube 100 into a cap or the retaining mechanism 58 (and then the container 52). The ribs 130 may also center the wick 60 such that a longitudinal axis of the wick 60 is coincident with the longitudinal axis 134 of the tube 100. The ribs 130 may also create equidistant columnar channels 131 of the same shape and size to provide even fluid distribution and flow to and around the wick 60.

Optionally, differently-sized columnar channels 131 may be created. Still further, the ribs 130 allow for variation in a diameter of the wick 60.

In illustrative embodiments, the ribs 130 have a width W that varies along a length L thereof, for example, the ribs 130 may have a width W at a center section 138 thereof that is greater than at a top end 140 or bottom end 142 thereof. A greater width W at a center section 138 than at top and/or bottom ends 140, 142 provides for ease in insertion of the wick 60 within the tube 100 and insertion of the wick 60 into the tube 100 from the bottom end 112 or a top end 144 while still retaining the wick 60 as described in detail above. While the length L of the ribs 130 is shown as being the same as a length of the tube 100, the length L of one or more of the ribs 130 may be less than the length of the tube 100, for example, the ribs 130 may end short of the bottom end 112 and/or the top end 144 of the tube 100.

In a further illustrative embodiment, the wick 60 may be formed in a helix, a star shape, or may have any other similar shape or feature(s) (such as splines) having a number of internal grooves formed therein that create the columnar channels 131 when an outer periphery of the wick 60 is disposed adjacent an inner periphery of the tube 100. In such an embodiment, the wick 60 may fit tightly by, for example, an interference or friction fit, within the tube 100 to provide the columnar channels 131. In another embodiment, the tube 100 may include one or more annular rings, helical ribs, and/or longitudinal ribs 130 that create specific spaces or volumes, create wick contact points, and/or control the flow of the compositions 53, 54 therethrough.

In other illustrative embodiments, for example, as seen in FIGS. 8 and 9, the tube 100 may include one or more vents 150. In an exemplary embodiment, the tube 100 may include a first vent 150a disposed in a bottom peripheral edge 152 of the tube 100 and/or a second vent 150b disposed in an upper peripheral edge 154 of the tube 100. In an illustrative embodiment, the vents 150a, 150b may be disposed about 180 degrees around the tube 100 from one another. Alternatively, the vents 150a, 150b may be disposed between 1 and 360 (aligned along the longitudinal axis 134) degrees around the tube 100 from one another. Still further, although one vent is shown in each of the bottom and upper peripheral edges 152, 154, any suitable number of vents may be disposed in the bottom and upper peripheral edges 152, 154, and/or the number of vents in each of the bottom and upper peripheral edges 152, 154 need not be the same. In illustrative embodiments, the vents 150a, 150b may have a semicircular shape. Alternatively, the vents 150a, 150b may have any other suitable shape. The vents 150a, 150b may ensure liquid flow through the bottom end 112 of the tube 100 and/or may prevent shut off at the top end 144 of the tube 100 where the tube 100 may potentially be in contact with or integral with the retaining mechanism 58 or another feature that supports the tube 100 and/or closes the neck 70 of the container 52. As can be seen in FIG. 8, a tube 100 of the present disclosure may include one or more ribs 130 and/or one or more vents 150.

Figure 10:
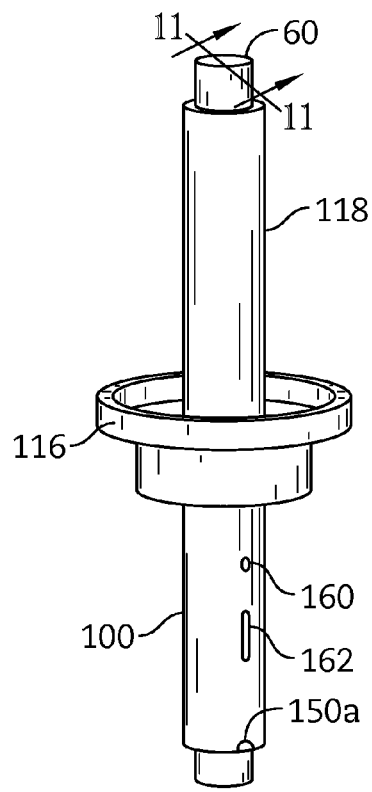
FIG. 10 is a top isometric view of a retaining mechanism including a cap portion and a sheath portion extending from the cap portion, a tube connected to or integral with the cap portion, and a wick held in position by the retaining mechanism and the tube, wherein the tube includes metering holes and slots.
Figure 11:
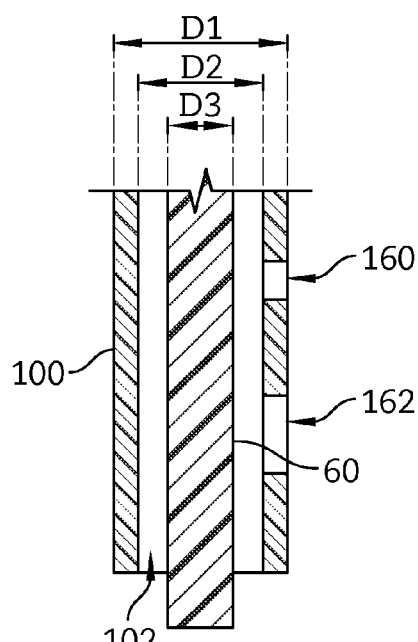
FIG. 11 is a partial cross-sectional view taken generally along the lines 11-11 of FIG. 10 and depicting a gap disposed between the tube and the wick.
Figure 12:
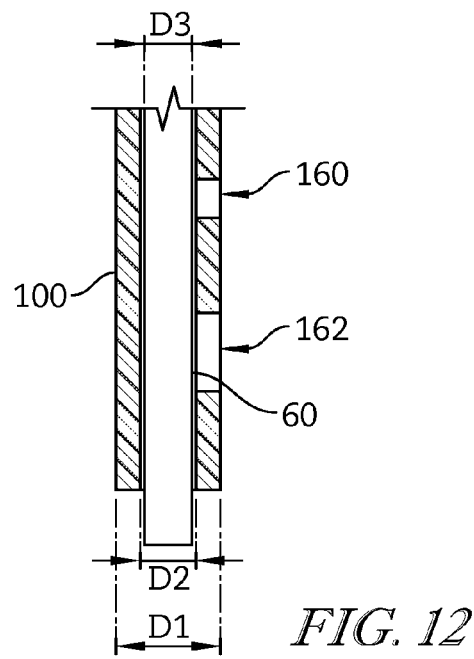
FIG. 12 is a partial cross-sectional view similar to that of FIG. 11 and depicting no gap formed between the tube and the wick of FIG. 10.

The emission of the first and second compositions 53, 54 (or more, if utilized) may be controlled or metered through the strategic placement of holes or slots in the tube 100. In an illustrative embodiment, as seen in FIGS. 10-12, the tube 100 may include one or more metering holes 160 and/or metering slots 162. The tube 100 may be integral with or otherwise connected to a retaining mechanism 58, as discussed in detail above. The metering holes and slots 160, 162 may control fluid phase mixing and/or timing of emission of the first and second compositions 53, 54 having different phases. As seen in FIGS. 11 and 12, the inner diameter D2 of the tube 100 may be greater than the outer diameter D3 of the wick 60 to create a gap 102 (FIG. 11), as discussed in detail above, or the outer diameter D3 of the wick 60 may be the same as or greater than the inner diameter D2 of the tube 100 to create an interference or friction fit therebetween (FIG. 12). Metering holes 160 or slots 162 may be utilized with any embodiments herein.

Figure 13:
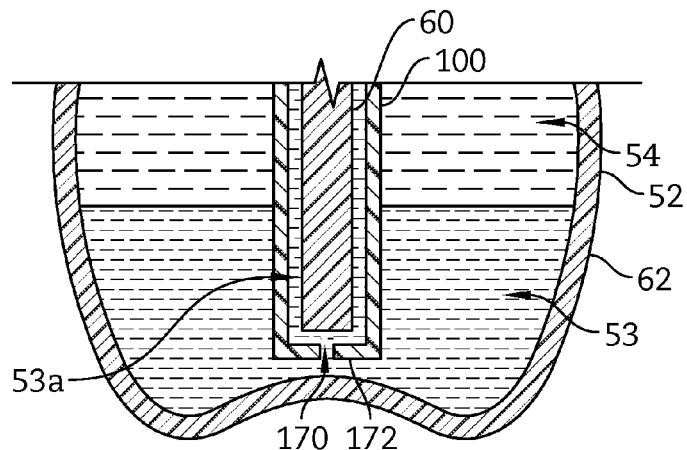
FIG. 13 is a partial cross-sectional view of a refill, for example, the refill of FIG. 3 implementing a further embodiment of a tube of the present disclosure.
Figure 14A:
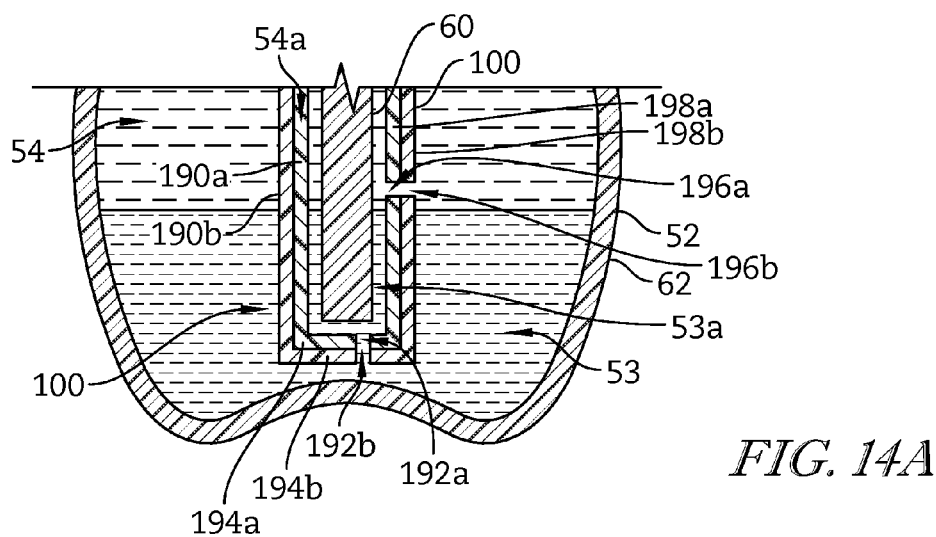
FIG. 14A is a partial cross-sectional view of a refill, for example, the refill of FIG. 3 including another embodiment of a tube of the present disclosure.
Figure 14B:
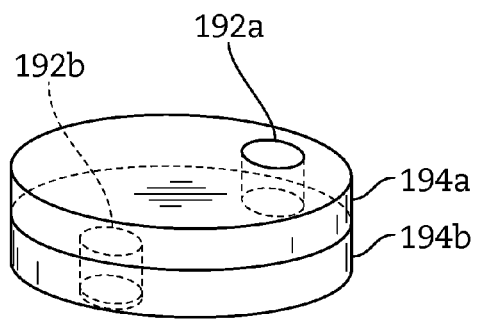
FIG. 14B is a top isometric view of a bottom portion of the tube of FIG. 14A depicting orifices in bottom ends of inner and outer tubes that can be aligned with one another to open the orifices and allow for flow of compositions therethrough or close the orifices for no flow of compositions therethrough.
Figure 15:
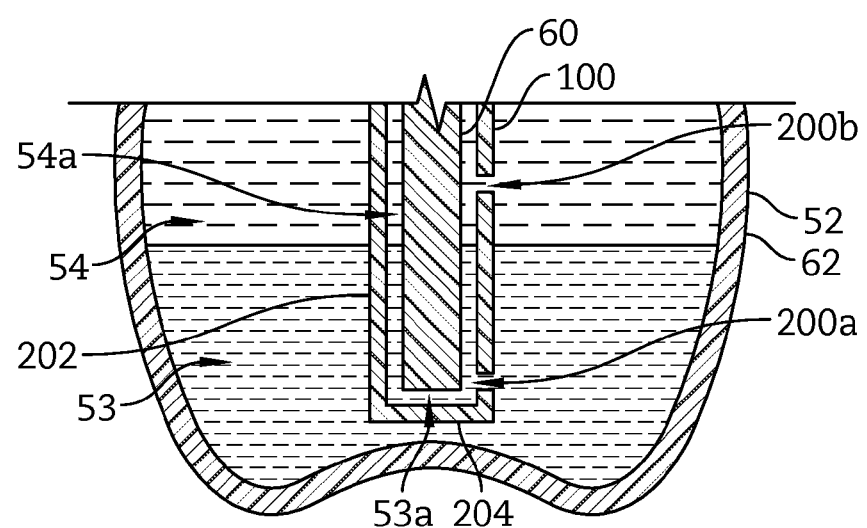
FIG. 15 is a partial cross-sectional view of a refill, for example, the refill of FIG. 3 including yet another embodiment of a tube of the present disclosure.

Other illustrative embodiments in which the placement of orifices in the tube 100 controls emission of the first and/or second compositions 53, 54 are depicted in FIGS. 13-15. In FIG. 13, the tube 100 is depicted as having a single orifice 170 through an otherwise closed bottom end 172 of the tube 100. If the tube 100 with wick 60 inserted therein is inserted into the container 52 with first and second compositions 53, 54 therein, the first composition 53 travels into the tube 100 and the first composition 53a within the tube 100 is absorbed by the wick 60. In this manner, the tube 100 and the wick 60 fill with the first composition 53a. Once substantially all of the first composition 53a within the wick 60 and the tube 100 and the first composition 53 within the container 52 are depleted, the second composition 54 travels into the tube 100 through the orifice 170 until the second composition 54 is substantially depleted.

In another embodiment with metering, as seen in FIGS. 14A and 14B, the tube 100 may be comprised of an inner tube 190a and an outer tube 190b. The inner and outer tubes 190a, 190b may include one or more orifices 192a, 192b in bottom ends 194a, 194b of the tubes 190a, 190b, wherein the orifices 192a, 192b may be aligned with one another for metering of the compositions 53, 54 into the tube 100. In illustrative embodiments, one or both of the inner and outer tubes 190a, 190b may be rotated relative to the other, as schematically seen in FIG. 14B, to close or partially close the orifices 192a, 192b. The inner and outer tubes 190a, 190b may additionally or alternatively include one or more orifices 196a, 196b in cylindrical side walls 198a, 198b of the tubes 190a, 190b that may be aligned with one another for metering of the compositions 53, 54 into the tube 100. In illustrative embodiments, one or both of the inner and outer tubes 190a, 190b may be rotated relative to the other to close or partially close the orifices 196a, 196b, as described above with respect to the orifices 192a, 192b. In one embodiment, alignment of the orifices 192a, 192b and the orifices 196a, 196b may occur at the same time. In another embodiment, alignment of the orifices 192a, 192b may not occur at the same time as alignment of the orifices 196a, 196b, such that only one set of orifices 192a, 192b or 196a, 196b may be open at a time. Rotation of the inner and outer tubes 190a, 190b relative to one another can be implemented electronically (e.g., such that the tubes 190a, 190b automatically rotate, for example, on a periodic or programmed basis) and/or the tubes 190a, 190b may be rotated manually by a user (e.g., using a knob, switch, lever, or other device that extends external to the refill).

Referring again to FIG. 14A, in an embodiment in which the alignment of the orifices 192a, 192b and 196a, 196b occurs at the same time, once the tube 100 with wick 60 inserted therein is inserted into the tube 100, the tube 100 begins to fill with the first and second compositions 53a, 54a. More particularly, the first composition 53 flows through the orifices 192a, 192b such that the first composition 53a fills a portion of the tube 100 at a level similar to a level of the first composition 53 in the container 52 and the second composition 54 flows through the orifices 196a, 196b such that the second composition 54a fills a portion of the tube 100 above the level of the first composition 53, 53a.

The second composition 54a within the wick 60 and the tube 100 is emitted first and the second composition 54 within the container 52 will continue to move into the tube 100 and be emitted from the wick 60 until the orifices 196a, 196b are closed. When the orifices 196a, 196b are closed, the second composition 54a within the wick 60 and the tube 100 and the first composition 53a within the wick 60 and the tube 100 will be emitted. Since the orifices 192a, 192b would also be closed, once the composition 53a within the wick 60 and the tube 100 is emitted, emission of the compositions will stop until the orifices 192a, 192b and 196a, 196b are again opened. When the orifices 192a, 192b and 196a, 196b are re-opened, the tube will again fill with the first and second compositions 53a, 54a (until a level of the second composition 54a in the container 52 is below the orifices 196a, 196b) and the process repeats. More specifically, the second composition 54a within the wick 60 and the tube 100 will be emitted and the second composition within the container 52 will be emitted until the orifices 192a, 192b and 196a, 196b are closed. The orifices 192a, 192b and 196a, 196b must be re-opened every time the first composition 53a within the wick 60 and the tube 100 is depleted to re-start the alternation/emission of compositions 53, 54.

In an embodiment in which the alignment of the orifices 192a, 192b and 196a, 196b does not occur at the same time, a user can fully or partially shut off the flow of either or both of the first and/or second compositions 53, 54 into the tube 100. In this manner, a user can switch or alternate between the compositions 53, 54 in any manner the user desires.

In another embodiment including metering, as seen in FIG. 15, any number of orifices 200a, 200b may be formed in a cylindrical side wall 202 of the tube 100. In the embodiment of FIG. 15, the tube 100 includes a closed bottom wall 204 and two orifices 200a, 200b formed in the cylindrical side wall 202. Once the tube 100 with wick 60 inserted therein is inserted into the container 52 with the compositions 53, 54, the compositions 53, 54 begin to flow through the orifices 200a, 200b into the tube 100. When equilibrium is reached, a level of the first composition 53 within the container 52 is substantially the same as a level of the first composition 53a within the tube 100. Additionally, the second composition 54a fills the tube 100 and the wick 60 above the level of the first composition 53a. The second composition 54a will be depleted from the wick 60 and the tube 100 until a level of the second composition 54 within the container is below the orifice 200b, in which case, the first composition 53a within the wick 60 and the tube 100 will be emitted and will continuously refill from the first composition 53 within the container 52 until the first composition 53 is substantially depleted. When the first composition 53 is substantially depleted (or below the orifice 200a), the second composition 54 will travel through the orifice 200a into the wick 60 for emission of the second composition 54.

As discussed above, each of the compositions 53, 54 (or more, if utilized) may include one or more dyes that may differentiate the compositions 53, 54 from one another. Dyes may be utilized in any of the embodiments disclosed herein such that each of the compositions 53, 54 changes the color of portions of the wick 60 occupied by the respective compositions 53, 54. In this manner, the color closest to a tip of the wick 60 will indicate which of the compositions 53, 54 is being emitted from the refill 51. Alternatively or additionally, a user may be able to discern from colors of the tube and/or colors within the tube which of the compositions 53, 54 is being emitted from the refill.

While the refills and methods of the present disclosure have been discussed in relation to the dispenser 50 of FIGS. 1-4, the methods of the present disclosure may be implemented within any dispenser capable of emitting compositions having one or more active ingredients. Further, while the embodiments of the present disclosure are discussed in relation to a particular refill, the principles of the present disclosure may be implemented with any refill. The principles of the present disclosure may be implemented within a refill that has been designed to control a volume and timing of emission of the different compositions, for example, the refill may be larger at a top or a bottom for greater or lesser volumetric ratio of multi-layer compositions.

In any of the embodiments herein, any number of tubes 100 and wick 60 may be present within a single refill 51. If multiple tubes 100 and wicks 60 are utilized, each of the tubes 100 and/or wicks 60 may be the same, one or more of the tubes 100 and/or wicks 60 may be the same, or none of the tubes 100 and/or wicks 60 may be the same.

While the tubes 100 and wicks 60 are depicted herein as being in a vertical orientation, any of the principles of the present disclosure may be utilized in conjunction with tubes 100 and/or wicks 60 that are disposed in other orientations, such as angled or a horizontal orientation.

While the wicks and tubes herein are shown and disclosed as being generally cylindrical, the principles of the present disclosure may be applied to wicks and tubes of all shapes and sizes. The wicks and/or tubes of the present disclosure may have cross-sectional shapes such as round, square-shaped, star-shaped, rectangular, oval, octagonal, hexagonal, pentagonal, or any other suitable cross-sectional shape or shapes. Still further, the principles of the present disclosure may be applied to wicks having any features, such as hollow wicks, splined wicks, helixed wicks, wicks with internal grooves and/or external ridges, or wicks with any other features. A size and/or shape of the tubes of the present disclosure also need not be the same as a size and/or shape of the wicks of the present disclosure. In an illustrative embodiment, a tube may have a round cross-sectional shape and a wick may have a star shape.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present disclosure provides refills, methods, and systems for emitting two or more compositions from a single refill. The refills, methods, and systems provide metering of two or more compositions and/or alternation of two or more compositions to prevent habituation and create a more pleasurable experience for a user.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A method of emitting two or more compositions, the method including the steps of:
providing a refill including a container having a body and first and second compositions disposed within the body within a single reservoir, such that the first and second compositions are substantially separated within the single reservoir;
emitting a first portion of the second composition;
emitting a portion of the first composition after the first portion of the second composition is emitted; and
emitting a second portion of the second composition.

2. The method of claim 1, wherein the step of emitting a portion of the first composition includes emitting substantially all of the first composition.

3. The method of claim 1, wherein the step of emitting a second portion of the second composition includes emitting the second composition until substantially all of the second compositions is depleted.

4. The method of claim 1, wherein the first portion of the second composition is emitted from within a tube, a portion of the first composition is emitted from within the tube and a remainder of the first composition is emitted from within the container, and the second portion of the second composition is emitted from within the container.

5. The method of claim 1, further including the step of providing a dispenser including a housing forming a chamber adapted to retain the refill containing two or more compositions and a heater disposed within the chamber.

6. The method of claim 1, wherein the second composition is disposed above and substantially separated from the first composition.

7. The method of claim 6, wherein after the step of emitting a second portion of the second composition, the first composition is again emitted and emission of the first and second compositions repeats.

8. The method of claim 1, wherein the second composition is disposed below and substantially separated from the first composition.

9. The method of claim 8, wherein after the step of emitting a second portion of the second composition, the first composition is again emitted and emission of the first and second compositions repeats.

10. A method of emitting two or more compositions, the method including the steps of:
providing a refill including a container having a body and first and second compositions disposed within the body such that the first and second compositions are substantially separated;
emitting a first portion of the second composition with a wick;
emitting a portion of the first composition with the wick after the first portion of the second composition is emitted; and
emitting a second portion of the second composition with the wick.

11. The method of claim 10, wherein the first and second compositions are disposed within a single reservoir within the container.

12. The method of claim 10, wherein the wick is disposed at least partially within a tube, with the tube extending into both of the first and second compositions within the container.

13. The method of claim 12, wherein the wick is at least partially spaced apart from an interior wall of the tube to provide one or more channels within the tube for flow of the first and second compositions around the wick.

14. The method of claim 12, wherein the tube is a first tube;
wherein the wick is also disposed at least partially within a second tube, with the second tube disposed at least partially within the first tube so that at least a portion of the wick is disposed within both of the first and second tubes; and
wherein the method further includes the step of controlling the emission of at least one of the first and second compositions by rotating one of the first and second tubes relative to the other of the first and second tubes.

15. A method of emitting two or more compositions, the method including the steps of:
providing a refill including a container having a body, a tube, and first and second compositions disposed within the body within a single reservoir, such that the first and second compositions are substantially separated within the single reservoir and the tube extends into both of the first and second compositions within the single reservoir;
emitting a first portion of the second composition from the container with a wick that is disposed at least partially within the tube; and
emitting a portion of the first composition, with the wick, after the first portion of the second composition is emitted.

16. The method of claim 15, wherein the wick is at least partially spaced apart from an interior wall of the tube to provide one or more channels within the tube for flow of the first and second compositions around the wick.

17. The method of claim 15, wherein the tube is a first tube;
wherein the wick is also disposed at least partially within a second tube, with the second tube disposed at least partially within the first tube; and
wherein the method further includes the step of controlling the emission of at least one of the first and second compositions by rotating one of the first and second tubes relative to the other of the first and second tubes.

18. The method of claim 17, wherein the first tube includes a first opening and the second tube includes a second opening; and
wherein rotating the one of the first and second tubes relative to the other of the first and second tubes at least one of opens, partially opens, closes, and partially closes at least one of the first opening and the second opening to control the emission of the at least one of the first and second compositions.

19. The method of claim 1, wherein each of the steps of emitting the first portion of the second composition, emitting the portion of the first composition, and emitting the second portion of the second composition uses a shared wick.

20. The method of claim 19, wherein the shared wick is disposed at least partially within a tube;
wherein the tube extends into both of the first and second compositions; and
wherein the first and second compositions are substantially separated within the tube.

* * * * *